US009138224B2

United States Patent
Matsutani et al.

(10) Patent No.: US 9,138,224 B2
(45) Date of Patent: Sep. 22, 2015

(54) BENDING METHOD OF MEDICAL SUTURE NEEDLE AND MEDICAL SUTURE NEEDLE

(75) Inventors: Kanji Matsutani, Utsunomiya (JP); Masaki Mashiko, Utsunomiya (JP); Yoshimasa Tochimura, Utsunomiya (JP)

(73) Assignee: MANI, INC., Utsunomiya-shi, Tochigi (JP)

( * ) Notice: Subject to any disclaimer, the term of this patent is extended or adjusted under 35 U.S.C. 154(b) by 1249 days.

(21) Appl. No.: 12/439,073

(22) PCT Filed: Aug. 29, 2007

(86) PCT No.: PCT/JP2007/066746
§ 371 (c)(1),
(2), (4) Date: Dec. 4, 2009

(87) PCT Pub. No.: WO2008/026630
PCT Pub. Date: Mar. 6, 2008

(65) Prior Publication Data
US 2010/0069956 A1 Mar. 18, 2010

(30) Foreign Application Priority Data
Aug. 29, 2006 (JP) .................................. 2006-231643

(51) Int. Cl.
*B21D 5/04* (2006.01)
*A61B 17/06* (2006.01)
(Continued)

(52) U.S. Cl.
CPC ............. *A61B 17/06066* (2013.01); *B21F 1/00* (2013.01); *B21G 1/08* (2013.01); *A61B 2017/00526* (2013.01); *A61B 2017/0608* (2013.01)

(58) Field of Classification Search
CPC .............. B21D 5/14; B21D 3/05; B21D 9/12; B21D 1/02; B21D 7/022; B21D 7/08; B21D 7/085; B21D 7/10; B21B 39/04; B21G 1/12; B21G 1/04; B21G 1/00; B21G 1/08; B41L 9/08; G11B 15/29; A61B 17/06066; A61B 2017/00526; A61B 2017/0608
USPC ........... 72/166–169, 127, 133, 192, 217, 251, 72/250, 428; 163/1, 5; 242/538.2; 226/181
See application file for complete search history.

(56) References Cited

U.S. PATENT DOCUMENTS

| 4,910,984 | A | * | 3/1990 | Young et al. .................... 72/14.7 |
| 4,935,029 | A | * | 6/1990 | Matsutani et al. ............. 606/223 |
| 4,976,727 | A | * | 12/1990 | Matsutani et al. ............. 606/223 |
| 5,431,036 | A | * | 7/1995 | Bogart ............................ 72/171 |
| 5,450,739 | A | * | 9/1995 | Bogart et al. ................... 72/133 |
| 5,526,666 | A | * | 6/1996 | Bogart et al. ................... 72/133 |
| 5,626,043 | A | * | 5/1997 | Bogart et al. ................... 72/133 |
| 7,065,999 | B2 | * | 6/2006 | Fukuchi et al. ................ 72/171 |

(Continued)

FOREIGN PATENT DOCUMENTS

| JP | 3-230836 A | 10/1991 |
| JP | 3-281025 A | 12/1991 |
| JP | 4-270021 A | 9/1992 |

*Primary Examiner* — Shelley Self
*Assistant Examiner* — Lawrence Averick
(74) *Attorney, Agent, or Firm* — Shlesinger, Arkwright & Garvey LLP

(57) ABSTRACT

A bending method for a straight needle-shaped material which has a thickness decreased from a body portion to a needle point that is inserted between a roller having a processing surface and a belt and is wound around the roller via a separating member. Then the roller is rotated and the belt is wound, thereby pressing and curving the straight needle-shaped material onto the processing surface. In a suture needle, a portion of a tip side including the needle point is formed as a non-restricted portion which is not restricted by the processing surface of the roller, and a portion except for the non-restricted portion is formed as a curved portion which is bent along the processing surface of the roller.

6 Claims, 3 Drawing Sheets

(51) Int. Cl.
  *B21F 1/00* (2006.01)
  *B21G 1/08* (2006.01)
  *B21B 39/02* (2006.01)
  *B44B 5/00* (2006.01)
  *A61B 17/00* (2006.01)

(56) References Cited

U.S. PATENT DOCUMENTS 7,662,170 B2 * 2/2010 Mashiko et al. ............... 606/222
2004/0025556 A1 * 2/2004 Klint et al. ..................... 72/130

* cited by examiner

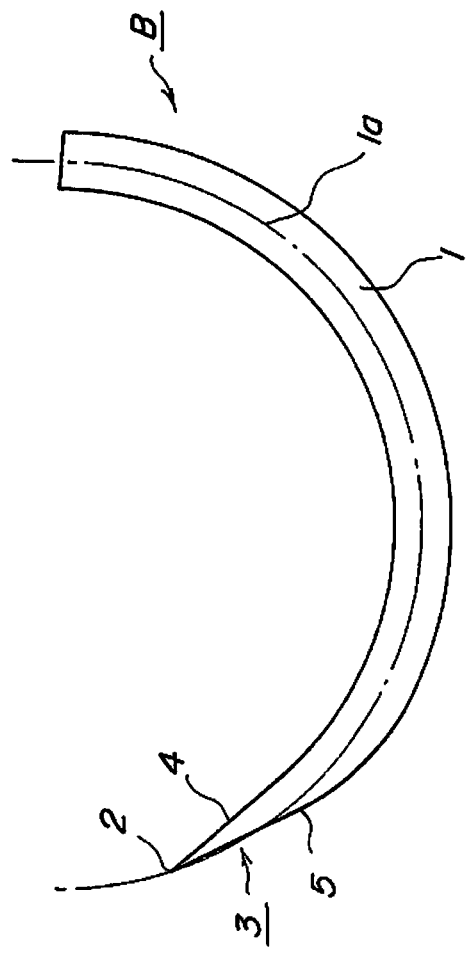
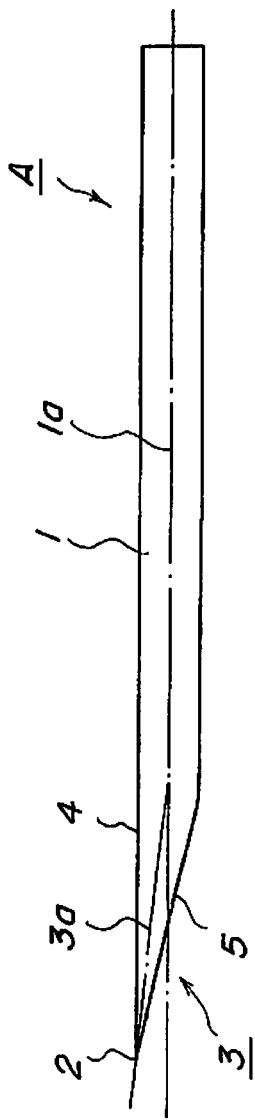
FIG. 1A
FIG. 1B

BENDING METHOD OF MEDICAL SUTURE NEEDLE AND MEDICAL SUTURE NEEDLE

TECHNICAL FIELD

The present invention relates to a bending method of a medical suture needle which has a thickness decreased from a body portion to a needle point and is curved such that the curvature of a shaft center of the body portion is as close to the curvature of the center of the thickness of the portion which has a thickness decreased from the body portion to the needle point as possible and to a medical suture needle.

BACKGROUND ART

There have been proposed medical suture needles which have various shapes (e.g., a straight needle and a curved needle) and dimensions corresponding to an applied portion. The curved needle is formed so as to be curved at a predetermined angle and radius. There have been proposed a round needle of circular cross-section and a cornered needle of polygonal cross-section.

The medical suture needle has a body portion held by a needle holder, a sharp needle point for penetrating a biotissue, and a needle point portion which has a thickness decreased from the body portion to the needle point. The body portion typically has a cross section formed in flat shape so as to be stably held by the needle holder.

In a bending method of a medical suture needle as described in Patent Document 1, there is used a bending device which has a cylindrical winding roll which defines the curved shape of the medical suture needle, an auxiliary roll which is pressingly contacted with the winding roll, and a metal belt arranged between the winding roll and the auxiliary roll. A straight needle-shaped material is inserted between the winding roll and the metal belt, and then the winding roll rotates a predetermined angle clockwise. The inserted straight needle-shaped material can be bent. The winding roll is rotated counterclockwise to take out the curved medical suture needle.

A bending method described in Patent Document 2 is preferably used for bending a medical suture needle with a blade which has a triangular cross section. In the bending method, an elastic member adheres to one surface configuring the triangular shape. The suture needle is arranged so as to bring the surface into contact with a cylindrical bending top. The suture needle is inserted between the bending top and a belt.

In the technique described in Patent Documents 1 and 2, a portion of the outer circumferential surface or one surface of the straight needle-shaped material is brought into contact with the surface of the cylindrical winding roll or the bending top. In this state, the straight needle-shaped material is pressed by the belt from the opposite side and is then bent. The bending shape of the medical suture needle is defined by the outer diameter of the winding roll or the bending top.

The bending shape of the medical suture needle is defined by the outer diameter of the winding roll or the bending top. This does not mean that the outer diameter of the winding roll or the bending top and the diameter of the curved inner surface of the medical suture needle are the same. Due to springback caused in the material of the medical suture needle, the diameter of the curved inner surface of the medical suture needle is typically larger than the outer diameter of the winding roll or the bending top.

[Patent Document 1] Japanese Patent Application Publication (JP-B) No. 07-004388
[Patent Document 2] Japanese Patent No. 2849143

DISCLOSURE OF THE INVENTION

Problems to be Solved by the Invention

Typically, the portion of about two-thirds of the suture needle from the needle point is held by the needle holder for suturing. When the biotissue is sutured using the curved medical suture needle, the needle point is difficult to penetrate the biotissue and the resistance immediately after the penetration of the needle point is high. Such problems are felt by a more skillful doctor. Actually, the curved medical suture needle having a uniform penetration resistance at suturing is desired to be developed.

An object of the present invention is to provide a bending method of a medical suture needle and a medical suture needle, which can satisfy the above requirement.

Means for Solving the Problems

The present inventors have performed various examinations and experiments to satisfy the above requirement. As a result of this, the present inventors have obtained some findings to make the present invention.

As described above, the curved medical suture needle has the curved shape along the surface of the cylindrical bending roller. The shaft center of the body portion which has substantially the same thickness is curved substantially uniformly with a dimension obtained by adding half of the thickness of the body portion to the radius of the bending roller as a radius. The curvature of the body portion becomes substantially the same.

The thickness of the needle point portion from the body portion to the needle point is decreased. A line corresponding to the dimension of half of the thickness of the needle point portion is an imaginary shaft center. The curvature of the imaginary shaft center is not the same and is continuously increased from the body portion to the needle point. The needle point is located inwardly (on the center side of an arc) from the extension line (on the arc having the same radius) of the shaft center of the uniformly curved body portion.

The suturing by the doctor at the penetration into the biotissue is performed along the curve of the body portion. Due to a subtle difference in the curvature from the needle point portion including the needle point to the body portion, the needle point portion including the needle point is bent from the early state in which the needle point penetrates the biotissue to the passage of the body portion. The doctor needs a force obtained by adding the force bending the needle point portion to the penetration resistance when the needle point passes through the biotissue.

Therefore, when at least the needle point is as close to the extension line of the shaft center of the curved body portion as possible, the resistance caused at the penetration into the biotissue can be reduced.

According to the present invention, a bending method of a medical suture needle in which a straight needle-shaped material which has a thickness decreased from a body portion to a needle point is inserted between a roller having a processing surface and a belt, and then the roller is rotated and the belt is wound so that the straight needle-shaped material is pressed onto the processing surface and is then curved, the method including: providing a separating member for separating the belt and the processing surface of the roller; and inserting the needle point of the straight needle-shaped material between the processing surface of the roller and the belt separated by the separating member, and then the roller is rotated and the belt is wound around the roller, thereby curving the straight needle-shaped material.

A medical suture needle in which a straight needle-shaped material which has a thickness decreased from a body portion to a needle point is inserted between a roller having a processing surface and a belt, and then the roller is rotated and the belt is wound so that the straight needle-shaped material is pressed onto the processing surface and is then curved, wherein a portion of a tip side including the needle point is formed as a non-restricted portion which is not restricted by the processing surface of the roller; and a portion except for the non-restricted portion is formed as a curved portion which is bent along the processing surface of the roller.

Effect of the Invention

In the bending method of a medical suture needle (hereinafter, called a "suture needle"), the belt and the processing surface of the roller are separated by the separating member. When the material is inserted between the belt and the roller in this state, the needlepoint of the inserted material is located in the gap between the belt and the roller separated by the separating member and is not pressed onto the processing surface of the roller by the belt.

Accordingly, the portion which includes the needlepoint and has a thickness corresponding to the separating dimension of the belt and the roller separated by the separating member (the needle point portion) is urged to the processing surface of the roller by the belt and is not strongly pressed onto the processing surface. The needle point portion is bent only by the belt and is not defined by the processing surface of the roller.

The bent needle point is located in the position where it is close to the extension line of the shaft center of the body portion from the position corresponding to the outer diameter of the roller. The needle point can be as close to the extension line of the shaft center of the curved body portion as possible.

In the suture needle of the present invention, a portion of the tip side including the needle point is formed as the non-restricted portion which is not restricted by the processing surface of the roller. The needle point can be as close to the extension line of the shaft center of the curved body portion as possible. Even if the doctor sutures the biotissue along the curve of the body portion, the needle point portion including the non-restricted portion is not bent. Therefore, the resistance can be reduced.

BRIEF DESCRIPTION OF THE DRAWINGS

FIG. 1(a) is a diagram for explaining a straight needle-shaped material and FIG. 1(b) is a diagram for explaining a curved suture needle;

EXPLANATION OF THE REFERENCE NUMERALS

Figure 2A:
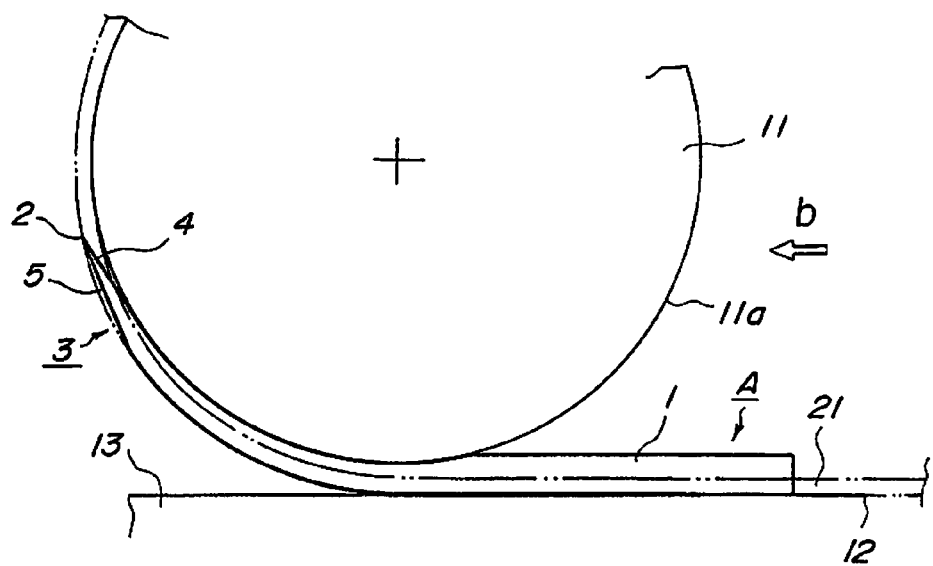
FIGS. 2(a) and 2(b) are diagrams for explaining a state of performing bending.

A: Material
B: Suture needle
1: Body portion
1a: Shaft center
2: Needle point
3: Needle point portion
3a: Axis line
4: Plane
5: Ridge
11: Roller
11a: Processing surface
12: Belt
13: Urging roller
14, 15: Belt pool
16, 19: Tension pulley
17: Nip roller
18: Guide roller
21: Separating member
22: Space

BEST MODE FOR CARRYING OUT THE INVENTION

Most preferred embodiments of a bending method of a suture needle and a suture needle according to the present invention will be described below.

In the bending method of a suture needle according to the present invention, a straight needle-shaped material formed to have a thickness decreased from a body portion to a needle point is inserted between a roller and a belt separated by a separating member. The roller is reciprocatively rotated a predetermined angle for pressingly contacting the belt with the roller. Without pressingly contacting a predetermined length portion including the needle point (a needle point portion) with the roller, a portion except for the needle point portion is wound around the roller for bending.

To perform the bending method of the present invention, there can be used a hitherto used bending device which has a roller, a belt wound around the roller, and an urging roller which urges the belt to the roller. The outer diameter of the roller is selected according to the specifications of the target suture needle. The bending device can bend suture needles having various curved shapes. The roller is selected in consideration of the curved shape of the target suture needle and springback caused according to the quality of the material Optimum bending can be performed.

The separating member is provided between the roller and the belt. The roller and the belt are separated without being directly contacted with each other. A space in which no bending force acts is configured. Therefore, the straight needle-shaped material is inserted between the belt and the roller separated by the separating member. The portion of the material which has a thickness smaller than that of the separating member (a portion of the needle point side including the needle point) exists in the space. No bending force is given from the belt, so that bending is not caused.

When the rotation of the roller progresses, the portion of the material which has a thickness larger than that of the separating member (the body portion and a portion of the needle point portion) is pressed onto the processing surface of the roller by the belt regardless of the existence of the separating member. The material is bent in the curved shape restricted by the processing surface of the roller. Therefore, the body portion which has a thickness larger than that of the separating member and a uniform thickness is bent at a uniform curvature.

With the progress of the bending of the body portion and a portion of the needle point portion according to the rotation of the roller, a portion of the needle point side including the needle point provided between the belt and the processing surface of the roller separated by the separating member exists in a tangent direction. A portion of the needle point side including the needle point is protruded from the space configured by the separating member to the belt. However, the belt is pressingly contacted with the separating member. The bending force by the belt relatively acts on the needle point side, and a portion of the needle point side including the needle point is bent by being restricted only by the belt without being restricted by the processing surface of the roller.

Therefore, this does not mean that the portion which has a thickness smaller than that of the separating member is not bent at all. Since bending is not restricted by the processing surface of the roller, an arc of an axis line which images the center of the thickness of the needle point portion from the needle point to the body portion can be close to an arc of a shaft center of the curved body portion.

In the present invention, the separating member has the function of separating the belt from the processing surface of the roller, and any separating member having the function can be used. Such separating member can be configured by a belt-shaped member which adheres to the surface of the belt opposite the processing surface of the roller. The separating member can also be configured by a belt-shaped member wound around the outer circumferential surface of the roller. Further, an annular groove can be formed in the outer circumferential surface of the roller, and its bottom surface can be configured as the processing surface. If the groove is formed in an urging roller 13, not in the roller 11, alternatively, the groove is formed in both the rollers, a belt 12 enters into the groove and is then bent so as not to restrict the needle point, thereby obtaining the same effect.

Other than special processing of the roller or the belt, the separating member can be configured by a pipe which covers the needle point portion or a thick coating layer which coats the needle point portion. Preferably, the pipe or the coating layer can be easily removed or separated after bending. Preferably, the separating member is appropriately selected and adopted among from some configurations.

The separating distance between the belt and the processing surface of the roller separated by the separating member (the height of the separating member) should be appropriately set according to the thickness of the suture needle, and cannot be uniquely set. Particularly, the height of the separating member is preferably selected, as needed, according to whether the suture needle is the round needle or the polygonal needle. When the suture needle is the triangular needle, the height of the separating member is preferably selected, as needed, according to whether the bottom surface of the triangular shape is inside the curve or the ridge is inside the curve.

In the findings of the present inventors, when the bottom surface of the triangular needle is brought into contact with the processing surface of the roller for bending, the height of the separating member is set to about half of the thickness of the body portion, so that the position of the needle point can be close to the extension line of the shaft center of the curved body portion in a preferable state.

The separating member need not be arranged over the substantially entire length of the straight needle-shaped material but may be arranged corresponding to a portion of the needle point side including the needle point. However, when the separating member is partially arranged, the position to insert the material is determined. This is not preferable in consideration of the working efficiency. Therefore, when the separating member is arranged on the belt side, the separating member is preferably arranged over the entire length of the belt. In addition, when the separating member is arranged on the roller side, the separating member is preferably arranged over the entire circumference of the outer circumferential surface of the roller.

The suture needle of the present invention can be obtained by performing the bending method of the present invention. The suture needle of the present invention is bent such that a portion of the needle point side including the needle point is not restricted by the processing surface of the roller. The suture needle of the present invention is bent such that the portion except for a portion of the needle point side is restricted by the processing surface of the roller.

The suture needle of the present invention is bent such that a portion of the needle point side including the needle point is not restricted by the processing surface of the roller. The curved shape of the axis line which images the center of the thickness of the portion does not have the shape corresponding to the radius of the processing surface. The curved shape has a radius larger than that of the processing surface and is close to the curved shape of the body portion bent by being restricted by the processing surface of the roller.

In the suture needle of the present invention, the sectional shape and dimension of the suture needle are not limited. There is intended the suture needle which is the round needle and the polygonal needle including the triangular needle and has the curved shape.

The quality of the material of the suture needle of the present invention is not limited. An austenitic stainless steel, a martensitic stainless steel, or a steel represented by a piano wire can be adopted selectively. However, in consideration of a rust problem and the compatibility with the biotissue, it is preferable to use a material in which the wire of the austenitic stainless steel is cold drawn to extend its tissue in fiber shape. The material is hardened with cold-working and has a high bending strength.

Example

A bending method of a suture needle and a suture needle according to this example will be described using the drawings. FIG. 1(*a*) is a diagram for explaining a straight needle-shaped material and FIG. 1(*b*) is a diagram for explaining a curved suture needle. FIGS. 2(*a*) and 2(*b*) are diagrams for explaining a state of performing bending. FIG. 3 is a diagram for explaining an example of a bending device preferable for performing a bending method of the present invention.

A straight needle-shaped material A will be described with FIG. 1(*a*). The material A illustrated in the drawing is configured as the material of the triangular needle having a blade. The material A has a body portion 1 having a uniform thickness, a needle point 2 which has a sharp tip suitable for penetrating the biotissue, and a needle point portion 3 which has a triangular cross section and has a thickness decreased from the body portion 1 to the needle point 2.

The length of the needle point portion 3 is appropriately set according to the shape and function of the suture needle. The length of the needle point portion 3 of the triangular needle with a blade is set in the range of about three to five times the thickness of the body portion. In the round needle in which the cross section of the needle point portion 3 is circular, the length of the needle point portion 3 is set in the range of about 10 to 15 times the thickness of the body portion 1.

The needle point portion 3 of the material A has a plane 4 which coincides with the extension line of the outer circumference of the body portion 1, and a ridge 5 tilted toward the tip portion of the plane 4. Blades which cut open the biotissue are formed on both sides of the plane 4 in a width direction. The ridge 5 is formed as a ridgeline which does not have the cutting open function. Therefore, the needle point 2 is located at the tip of the plane 4, not on the extension line of a shaft center 1*a* of the body portion 1.

The shaft center 1a of the body portion 1 of the material A is a straight line. An axis line 3a of the needle point portion 3 which is imaged by continuing the center of the thickness of the needle point portion 3 intersects the shaft center 1a in the position corresponding to the boundary between the body portion 1 and the needle point portion 3.

Next, an example of the bending device will be described with FIG. 3. In the drawing, the roller 11 has an outer diameter corresponding to the curved shape of the suture needle. The outer circumferential surface of the roller 11 is a processing surface 11a. The belt 12 is wound around the roller 11 via a later-described separating member 21 and is urged to the roller 11 by the urging roller 13.

The belt 12 is configured to be long. The unused belt 12 is supplied from a belt pool 14. The belt 12 is urged to the roller 11 by the urging roller 13 to bend the material A. The belt 12 which has performed bending once is deformed corresponding to the shape of the material A and cannot be reused. Therefore, the used belt 12 is wound around a belt pool 15.

The belt 12 is given a tension by a tension pulley 16 in the path from the belt pool 14 to the rollers 11 and 13. The belt 12 is nipped between a pair of nip rollers 17 so as to be moved in a direction close to and away from the roller 11. The path from the rollers 11 and 13 to the belt pool 15 is defined by a guide roller 18. The belt 12 is given a tension by a tension pulley 19.

The rollers 11 and 13 are controlled so as to be synchronized and to be rotated in the arrow a direction and the arrow b direction. Further, the nip roller 17 is controlled so as to eliminate the slack of the belt 12 with the rotation of the roller 11 in the arrow a direction and to eliminate the action of the tension onto the belt 12 with the rotation of the roller 11 in the arrow b direction. When the rollers 11 and 13 are rotated in the arrow a direction, the material A is bent. When the rollers 11 and 12 are rotated in the arrow b direction, the bent material A can be discharged.

Figure 2B:
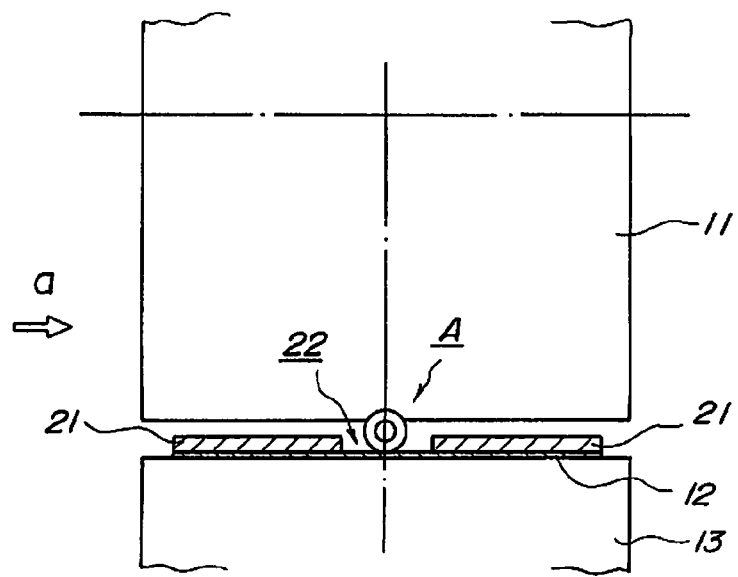
Figure 3:
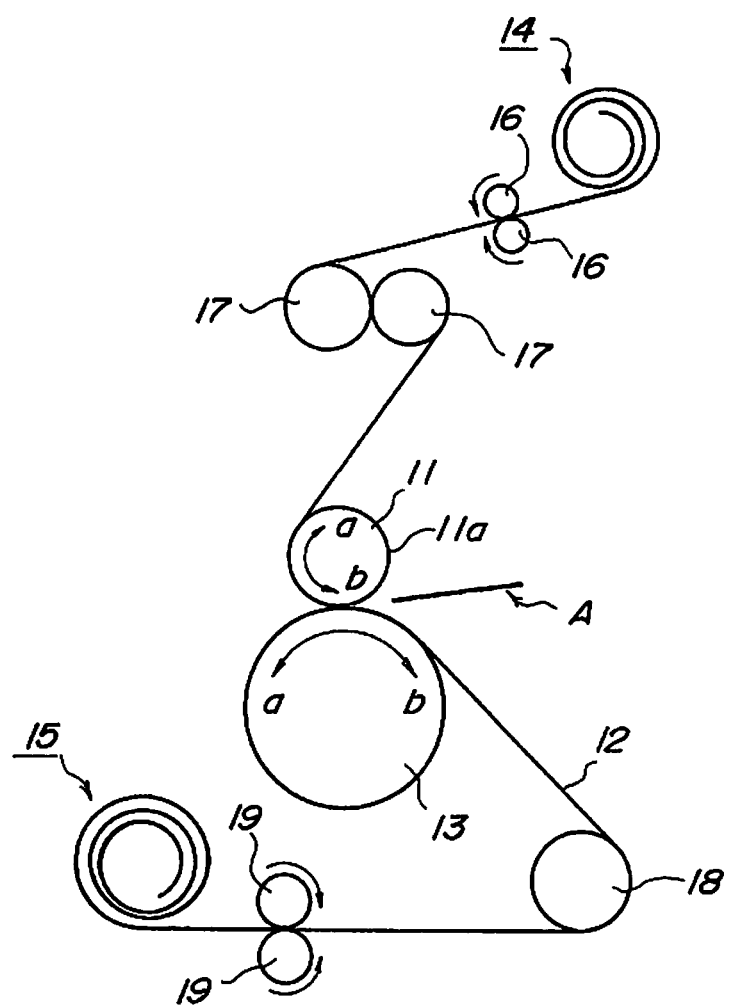
FIG. 3 is a diagram for explaining an example of a bending device preferable for performing a bending method of the present invention.

As illustrated in FIG. 2(b), the pair of belt-shaped separating members 21 which configure the separating means are arranged on the surface of the belt 12 opposite the roller 11. The thickness of the separating members 21 is set to the largest thickness or less of the material A which at least has a thickness decreased to the needle point. The separating members 21 adhere to the ends of the belt 12 in a width direction along a longitudinal direction. A space 22 which inserts the material A between the separating members 21 is configured.

Next, a procedure of performing the bending method of the material A according to this example will be described. In the state before the material A is bent, the belt 12 is wound around the roller 11 so as to be separated from the roller 11 by the thickness of the separating members 21. That is, the belt 12 is not directly wound around the roller 11. The space 22 is configured by the belt 12, the pair of separating members 21, and the processing surface 11a of the roller 11.

The plane 4 of the material A is directed toward the processing surface 11a of the roller 11 to insert the needle point 2 into the space 22. The inserted needle point 2 holds the free state in the space and cannot be pressed by the belt 12. Therefore, the portion which includes the needle point 2 and has a thickness smaller than that of the separating members 21 is pressingly contacted with the processing surface 11a and is configured as a non-restricted portion which is not restricted by the processing surface 11a. The portion except for the non-restricted portion of the material is restricted by the belt 11 and the roller 12 and is a curved portion which is bent along the processing surface of the roller 12. If the elasticity of the belt 11 and the roller 12 is not considered, the portion of the material A which has a thickness decreased to the needle point and has the same thickness as that of the separating members 21 becomes the boundary portion between the non-restricted portion and the curved portion.

When the roller 11 and the urging roller 13 are rotated from the above state in the arrow a direction, the material A is moved in the same direction with the rotation. With this, the portion of the needle point portion 3 of the material A which has a thickness larger than that of the separating members 21 enters into the space 22. Accordingly, the portion of the needle point portion 3 which has a thickness larger than that of the separating members 21 is nipped between the belt 12 urged by the roller 11 and the urging roller 13. The plane 4 is brought into contact with the processing surface 11a of the roller 11, and the ridge 5 is urged to the urging roller 13 via the belt 12, so that bending is performed with reference to the contacting surface of the plane 4 and the processing surface 11a.

With the progress of the bending of the needle point portion 3, the needle point 2 holds the straight needle shape as the starting point of the bending (the portion of the needle point portion 3 which has substantially the same thickness as that of the separating members 21). As a result, the needle point 2 is moved in the space 22 in the direction of the belt 12. The movement is accompanied by the bending caused in the portion of the needle point portion 3 which has a thickness larger than that of the separating members 21 and is not forced by the roller 11 or the belt 12.

When the needle point 2 or its vicinity is brought into contact with the belt 12, the belt 12 in the contacted portion is not urged by the urging roller 13 in the direction of the roller 11. A force according to the tension given by the tension pulley 16 and the rigidity of the belt 12 itself acts on the needle point 2 or its vicinity. The force is changed according to the progress of the bending from the needle point portion 3 to the body portion 1 and is changed according to the conditions of the outer diameter dimension of the roller 11 and the material A.

Therefore, the tip side including the needle point 2 of the material A (the portion of the needle point portion 3 which has a thickness smaller than that of the separating members 21 from the needle point 2) is slightly bent by the belt 12 or is hardly bent.

With the following rotation of the roller 11 and the urging roller 13 in the arrow a direction, the bending of the body portion 1 of the material A progresses. The bending at this time is restricted by the processing surface 11a of the roller 11 so as to configure the curved portion. When the roller 11 and the urging roller 13 are rotated a predetermined angle in the arrow a direction, the bending of the material A is completed. Thereafter, when the roller 11 and the urging roller 13 are rotated in the arrow b direction, the material A is bent with the rotation to discharge a curved suture needle B.

As illustrated in FIG. 1(a), the curved shape of the suture needle B discharged from between the roller 11 and the belt 12 is slightly changed by springback. The suture needle B has the curved shape corresponding to the processing surface 11a of the roller 11 from the portion of the needle point portion 3 which has a thickness larger than that of the separating members 21 to the body portion 1.

Then, the portion which includes the needle point 2 and has a thickness smaller than that of the separating members 21 is slightly bent by the belt 12 or holds the substantially straight needle-shape without being restricted by the processing surface 11a of the roller 11. Accordingly, the needle point 2 holds the position close to the extension line of the shaft center 1a of the curved body portion 1.

Particularly, if the thickness of the separating members 21 is set to substantially the same value as the dimension of the shaft center 1a of the body portion 1 of the material A, the position of the needle point 2 substantially coincides with the extension line of the substantially shaft center 1a. In this embodiment, the material A is processed in the space 22 between the pair of separating members 21. Three or more separating members 21 may be provided to create a plurality of spaces to process the plurality of materials A at the same time.

INDUSTRIAL APPLICABILITY

In the bending method according to the present invention, the suture needle which has a thickness decreased from the body portion to the needle point can be close to the curve with reference to the shaft center, not to the curved shape with reference to the processing surface of the roller. Therefore, the bending method according to the present invention is advantageously used for the bending of the suture needle regardless of the sectional shape or the shape of the needle point portion.

The invention claimed is:

1. A bending method of a medical suture needle in which a straight needle-shaped material which has a thickness decreased from a body portion to a needle point is inserted between a roller having a processing surface and a belt, and then the roller is rotated and the belt is wound on the processing surface so that the straight needle-shaped material is pressed onto the processing surface and is then curved, the method comprising the steps of:
    providing a belt-shaped separating member between the belt and the processing surface of the roller,
    separating the belt and the processing surface of the roller without directly contacting each other by the belt-shaped separating member which has a predetermined thickness smaller than the largest thickness of the material provided into a space between the belt and the roller, so that the space is configured in which no bending force acts against the needle point from the processing surface of the roller even when a portion of the belt corresponding to the needle point is completely wound on the processing surface;
    inserting the needle point of the straight needle-shaped material into the space between the processing surface of the roller and the belt separated by the belt-shaped separating member; and
    rotating the roller and winding the belt around the roller with the needle point kept in the space, thereby curving the straight needle-shaped material.

2. The bending method of a medical suture needle according to claim 1, wherein the belt-shaped separating member has a plurality of separating members, and the material is inserted into the space between the separating members and is then curved.

3. The bending method of a medical suture needle according to claim 1, wherein the belt-shaped separating member is fixed to the belt.

4. The bending method of a medical suture needle according to claim 1, wherein the belt-shaped separating member is fixed to the roller.

5. The bending method of a medical suture needle according to claim 1, wherein the belt-shaped separating member is a groove provided in the belt or the processing surface of the roller.

6. A bending method of a medical suture needle in which a straight needle-shaped material which has a thickness decreased from a body portion to a needle point is inserted between a roller having a processing surface and a belt, and then the roller is rotated and the belt is wound on the processing surface so that the straight needle-shaped material is pressed onto the processing surface and is then curved, the method comprising the steps of:
    inserting the needle point of the straight needle-shaped material into a groove configuring a space in which no bending force acts against the needle point from the processing surface of the roller even when a portion of the belt corresponding to the needle point is completely wound on the processing surface, the groove being provided in the belt or the processing surface of the roller; and
    rotating the roller and winding the belt around the roller with the needle point kept in the space, thereby curving the straight needle-shaped material.

* * * * *